(12) United States Patent
Ren et al.

(10) Patent No.: US 10,827,921 B2
(45) Date of Patent: Nov. 10, 2020

(54) IRIS EDGE DETECTION IN OPTICAL COHERENCE TOMOGRAPHY

(71) Applicant: Novartis AG, Basel (CH)

(72) Inventors: Hugang Ren, Cypress, CA (US); Muhammad K. Al-Qaisi, Ladera Ranch, CA (US)

(73) Assignee: Alcon Inc., Fribourg (CH)

( * ) Notice: Subject to any disclaimer, the term of this patent is extended or adjusted under 35 U.S.C. 154(b) by 143 days.

(21) Appl. No.: 16/202,271

(22) Filed: Nov. 28, 2018

(65) Prior Publication Data

US 2019/0159670 A1 May 30, 2019

Related U.S. Application Data

(60) Provisional application No. 62/591,563, filed on Nov. 28, 2017.

(51) Int. Cl.
| | | |
|---|---|---|
| *A61B 3/12* | (2006.01) | |
| *A61B 3/10* | (2006.01) | |
| *A61B 3/00* | (2006.01) | |
| *G06K 9/00* | (2006.01) | |

(52) U.S. Cl.
CPC ............ *A61B 3/102* (2013.01); *A61B 3/0025* (2013.01); *G06K 9/0061* (2013.01); *G06K 9/00597* (2013.01)

(58) Field of Classification Search
CPC .. A61B 3/102; A61B 3/10; A61B 3/12; A61B 3/1216

USPC ......................................... 351/206, 246, 205
See application file for complete search history.

(56) References Cited

U.S. PATENT DOCUMENTS

| | | | |
|---|---|---|---|
| 5,644,642 A | 7/1997 | Kirschbaum | |
| 2011/0299034 A1* | 12/2011 | Walsh ................ | A61B 3/0091 351/206 |
| 2015/0042949 A1 | 2/2015 | Jeglorz et al. | |
| 2017/0119247 A1 | 5/2017 | Walsh et al. | |

OTHER PUBLICATIONS

Williams, et al., "Fast segmentation of anterior segment optical coherence tomography images using graph cut" Eye Vis. (2015) 2:1.

* cited by examiner

*Primary Examiner* — Hung X Dang

(57) ABSTRACT

A-lines are obtained from an OCT scan of the eye, some of which pass through the iris and the lens and some of which pass through the lens but not the iris. An interface is detected from the A-lines; at least some of this interface is assumed to correspond to either the anterior or posterior of the iris. For each A-line, a first metric is derived from pixels near the detected first interface, such that the first metric reflects an OCT signal intensity associated with the interface, and a second metric is derived from pixels further from the interface, such that the second metric reflects OCT signal attenuation below the detected interface. An attenuation parameter is calculated for each A-line, based on the first and second metrics, and the iris's edge is detected by determining whether each A-line passes through the iris, based on the attenuation parameter.

24 Claims, 12 Drawing Sheets

IRIS EDGE DETECTION IN OPTICAL COHERENCE TOMOGRAPHY

TECHNICAL FIELD

Embodiments disclosed herein are related to devices, systems, and methods for detecting features of an iris using an Optical Coherence Tomography (OCT) system.

BACKGROUND

Current ophthalmic refractive surgical methods, such as cataract surgery, intra-corneal inlays, laser-assisted in situ keratomileusis (LASIK), and photorefractive keratectomy (PRK), rely on ocular biometry data to prescribe the best refractive correction. Historically, ophthalmic surgical procedures used ultrasonic biometry instruments to image portions of the eye. In some cases, these biometric instruments generated a so-called A-scan of the eye: an acoustic echo signal from all interfaces along an imaging axis that was typically aligned with an optical axis of the eye: either parallel with it, or making only a small angle. Other instruments generated a so-called B-scan, essentially assembling a collection of A-scans, taken successively as a head or tip of the biometry instrument was scanned along a scanning line. This scanning line was typically lateral to the optical axis of the eye. These ultrasonic A- or B-scans were then used to measure and determine biometry data, such as an ocular axial Length, an anterior depth of the eye, or the radii of corneal curvature.

In some surgical procedures, a second, separate keratometer was used to measure refractive properties and data of the cornea. The ultrasonic measurements and the refractive data were then combined in a semi-empirical formula to calculate the characteristics of the optimal intra-ocular lens (IOL) to be prescribed and inserted during the subsequent cataract phaco surgery.

More recently, ultrasonic biometry devices have been rapidly giving way to optical imaging and biometry instruments that are built on the principle of Optical Coherence Tomography (OCT). OCT is a technique that enables micron-scale, high-resolution, cross-sectional imaging of the human retina, cornea, or cataract. OCT technology is now commonly used in clinical practice, with such OCT instruments are now used in 80-90% of all IOL prescription cases. Among other reasons, their success is due to the non-contact nature of the imaging and to the higher precision than that of the ultrasound biometers.

Even with these recent advances, however, substantial further growth and development is needed for the functionalities and performance of biometric and imaging instruments.

SUMMARY

Iris detection, which includes detecting the edge of the iris so as to distinguish between the iris and the anterior lens, has previously been done by examining the OCT signal strength in OCT image data. In normal eyes, the OCT signal of the iris is often stronger than that of other tissues around it. However, in pathological eyes, such as dense cataract, the OCT signal of the lens can be strong too. Accordingly, iris detection based on OCT signal strength is not robust enough in clinical settings, where a variety of cataract conditions happen in the eye. The techniques disclosed herein use OCT measurements to exploit the intrinsic physical property difference between the iris and the lens, and can therefore provide robust detection of the iris's edge in clinical settings.

According to several embodiments described in detail below, A-lines are obtained from an OCT scan of the eye, some of which pass through the iris and the lens and some of which pass through the lens but not the iris. An interface is detected from the A-lines; at least some of this interface is assumed to correspond to either the anterior or posterior of the iris. For each A-line, a first metric is derived from pixels near the detected first interface, such that the first metric reflects an OCT signal intensity associated with the interface, and a second metric is derived from pixels further from the interface, such that the second metric reflects OCT signal attenuation below the detected interface. An attenuation parameter is calculated for each A-line, based on the first and second metrics, and the iris's edge is detected by determining whether each A-line passes through the iris, based on the attenuation parameter.

More particularly, embodiments of the presently disclosed techniques include a method for detecting an edge of an iris in optical coherence tomography (OCT) imaging of an eye, where the method comprises obtaining OCT data obtained from a scan of the eye, the OCT data comprising a plurality of A-lines, some of which pass through the iris and the lens of the eye and some of which pass through the lens but not the iris. The method further includes detecting a first interface extending across adjacent A-lines, wherein at least a portion of the detected first interface is assumed to correspond to either the anterior surface or posterior surface of the iris, and determining, for each of the adjacent A-lines, a first metric derived from one or more A-line pixels near the detected first interface, such that the first metric reflects an OCT signal intensity associated with the first interface;

The method still further includes determining, for each of the adjacent A-lines, a second metric derived from one or more A-line pixels further from the detected first interface than the one or more A-line pixels used to derive the first metric, such that the second metric reflects OCT signal attenuation at a point or points posterior to the detected first interface, and calculating an attenuation parameter for each of the adjacent A-lines, based on the first and second metrics. Finally, the method includes determining, for each of the adjacent A-lines, whether the A-line passes through the iris, by comparing the attenuation parameter to a threshold value. In some embodiments, a visual representation of the OCT data is displayed, the visual representation including an indication of the iris edge, based on the determining, for each A-line, of whether the A-line passes through the iris.

Also described in detail below are embodiments of OCT imaging apparatus configured to carry out the method summarized above, or variants thereof.

DETAILED DESCRIPTION

In the following description, specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

Figure 1:
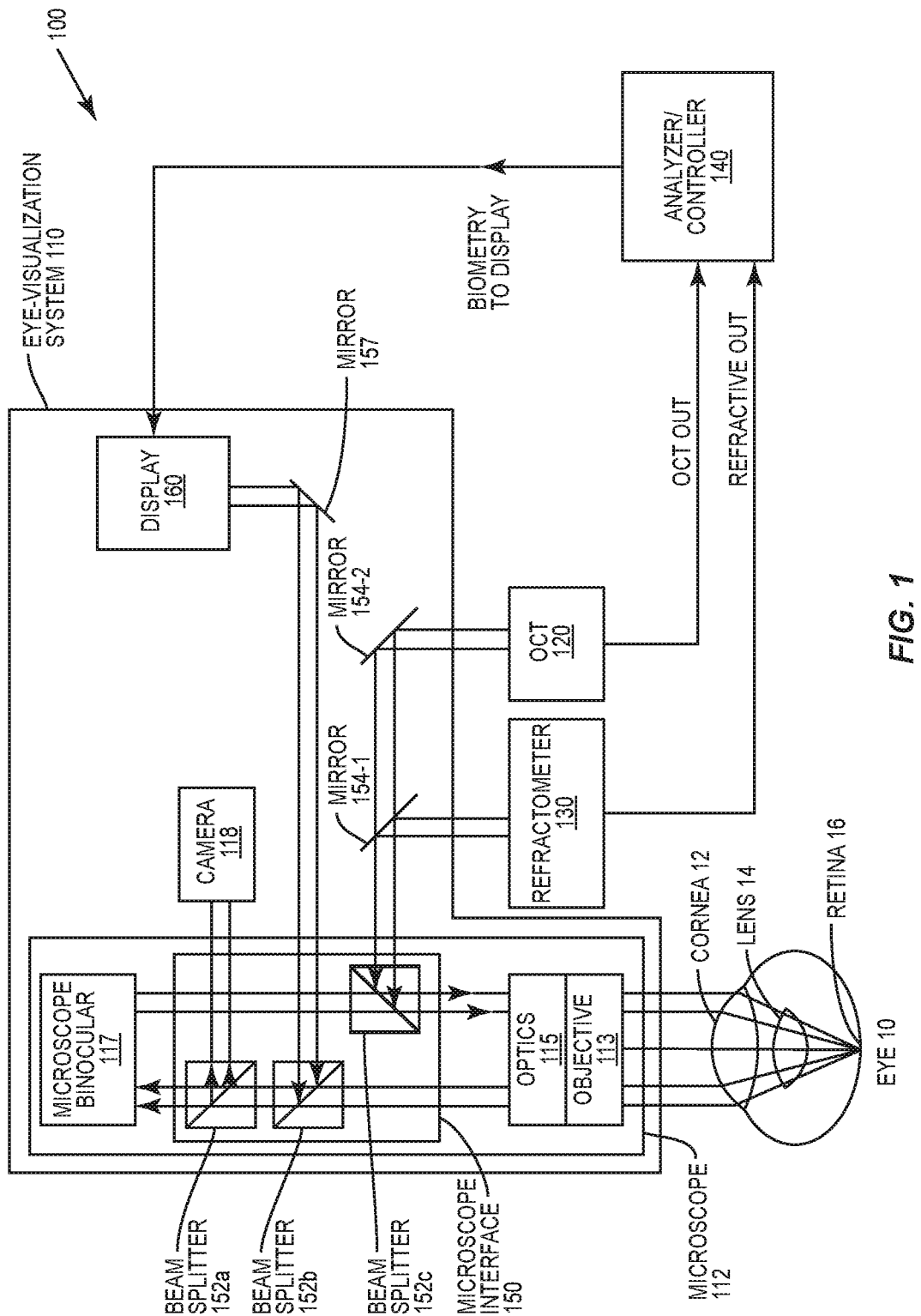
FIG. 1 is a diagram illustrating an Optical Coherence Tomography (OCT) system.

Embodiments of the presently disclosed techniques and apparatus may be employed in both microscope-mounted and microscope-integrated Optical Coherence Tomography (OCT) systems. FIG. 1 illustrates an example of a microscope-integrated OCT system 100, and is presented to illustrate the basic principles of OCT. It will be appreciated that OCT equipment configured to carry out the techniques described herein may vary from the example illustrated in FIG. 1 in various ways that are already known to the industry.

System 100 includes an eye-visualization system 110, configured to provide a visual image of an imaged region in an eye 10, an Optical Coherence Tomographic (OCT) imaging system 120, configured to generate an OCT image of the imaged region; a refractometer 130, configured to generate a refractive mapping of the imaged region; and an analyzer 140, configured to determine refractive characteristics of the eye based on the OCT image and the refractive mapping. It will be appreciated that the OCT imaging system 120, the refractometer 130, and the analyzer/controller 140 can be integrated into the eye visualization system 110.

Figure 2:
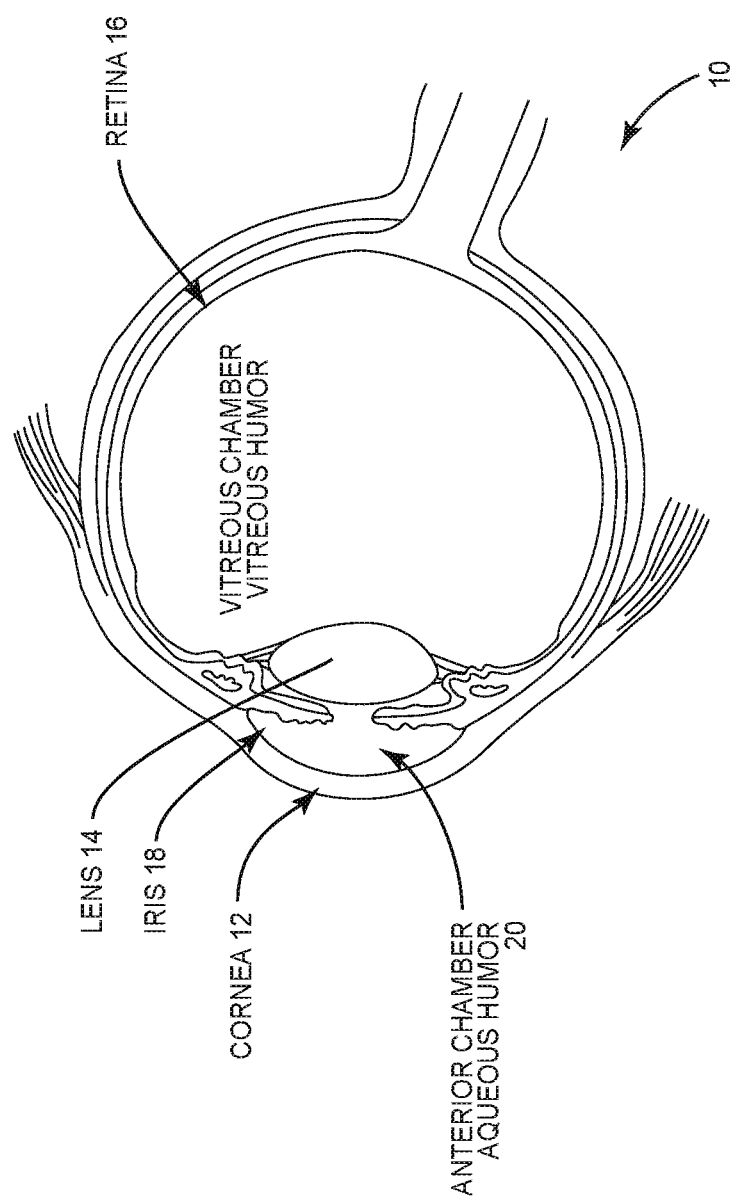
FIG. 2 is a schematic diagram of an eye.

The imaged region can be a portion or a region of the eye 10, such as a target of a surgical procedure. FIG. 2 is a cross sectional diagram showing features of an eye 10 in more detail than shown in FIG. 1. In a corneal procedure, the imaged region can be a portion of a cornea 12. In a cataract surgery, the imaged region can be a capsule (or capsular bag surrounding the natural lens 14) and the (crystalline) lens 14 of the eye. The imaged region may also include the anterior chamber 20 of the eye, the cornea 12, the lens 14, and the iris 18. Alternatively, the imaged region may cover the full eye, including the cornea 12, the lens 14, the iris 18, and the retina 16. In a retinal procedure, the imaged region can be a region of the retina 16. Any combination of the above imaged regions can be an imaged region as well.

The eye-visualization system 110 can include a microscope 112. In some embodiments, it can include a slit-lamp. The microscope 112 can be an optical microscope, a surgical microscope, a video-microscope, or a combination thereof. In the embodiment of FIG. 1, the eye-visualization system 110 (shown in thick solid line) includes the surgical microscope 112, which in turn includes an objective 113, optics 115, and a binocular or ocular 117. The eye-visualization system 110 can also include a camera 118 of a video microscope.

System 100 further includes the Optical Coherence Tomographic (OCT) imaging system 120. The OCT imaging system 120 can generate an OCT image of the imaged region. The OCT imaging system can be configured to generate an A-scan or a B-scan of the imaged region. The OCT image or image information can be outputted in an "OCT out" signal that can be used by analyzer 140, for example, in combination with an outputted "Refractive out" signal to determine biometric or refractive characteristics of the eye.

OCT imaging system 120 can include an OCT laser operating at a wavelength range of 500-2,000 nm, in some embodiments at a range of 900-1,400 nm. The OCT imaging system 120 can be a time-domain, a frequency-domain, a spectral-domain, a swept-frequency, or a Fourier Domain OCT system 120.

In various embodiments, part of the OCT imaging system 120 can be integrated into the microscope, and part of it can be installed in a separate console. In some embodiments, the OCT portion integrated into the microscope can include only an OCT light source, such as the OCT laser. The OCT laser or imaging light, returned from the eye, can be fed into a fiber and driven to a second portion of the OCT imaging system 120, an OCT interferometer outside the microscope. The OCT interferometer can be located in a separate console, in some embodiments, where suitable electronics are also located to process the OCT interferometric signals.

The OCT laser may have a coherence length that is longer than an extent of an anterior chamber of the eye, such as the distance between a corneal apex to a lens apex. This distance is approximately 6 mm in most patients, thus such embodiments can have a coherence length in the 4-10 mm range. Other embodiments can have a coherence length to cover an entire axial length of the eye, such as 30-50 mm. Yet others can have an intermediate coherence length, such as in the 10-30 mm range, finally some embodiments can have a coherence length longer than 50 mm. Some swept-frequency lasers are approaching these coherence length ranges. Some Fourier Domain Mode Locking (FDML) lasers, vertical-cavity surface-emitting laser (VCSEL)-based, polygon-based or MEMS-based swept lasers are already capable of delivering a laser beam with a coherence length in these ranges.

The example illustrated as system 100 further includes a refractometer 130 to generate a refractive mapping of the imaged region. The refractometer 130 may be any of the widely used types, including a laser ray tracer, a Shack-Hartmann, a Talbot-Moire, or another refractometer. The refractometer 130 can include a wavefront analyzer, an aberration detector, or an aberrometer. Some references use these terms essentially interchangeably or synonymously. A dynamic range of the refractometer 130 can cover both phakic and aphakic eyes, i.e., the eyes with and without the natural lens.

In some systems, the OCT imaging system 120 and the refractometer 130 can be integrated via a microscope interface 150 that can include a beam splitter 152c to provide an optical coupling into the main optical pathway of the microscope 112 or slit-lamp. A mirror 154-1 can couple the light of the refractometer 130 into the optical path, and a mirror 154-2 can couple the light of the OCT 120 into the optical path. The microscope interface 150, its beam splitter 152c, and mirrors 154-1 and 154-2 can integrate the OCT imaging system 120 and the refractometer 130 with the eye-visualization system 110.

In some embodiments, where the OCT imaging system 120 operates in the near infrared (IR) range of 900-1,400 nm, and the refractometer operates in the 700-900 nm range, the beam splitter 152c can be close to 100% transparent in the visible range of 400 nm-700 nm, and close to 100% reflective in the near-IR range of 700-1,400 nm range for high efficiency and low noise operations. Likewise, in a system where the mirror 154-1 redirects light into the refractometer 130, the mirror 154-1 can be close to 100% reflective in the near IR range of 700-900 nm, and the mirror 154-2 can be close to 100% refractive in the near IR range of 900-1,400 nm, redirecting to the OCT imaging system 120. Here, "close to 100%" can refer to a value in the 50-100% range in some embodiments, or to a value in the 80-100% range in others. In some embodiments, the beam splitter 152c can have a reflectance in the 50-100% range for a wavelength in the 700-1,400 nm range, and a reflectance in the 0-50% range for a wavelength in the 400-700 nm range.

FIG. 1 shows that the system 100 can include a second beam splitter 152b, in addition to the beam splitter 152c. The beam splitter 152c directs light between the objective 113 and the integrated OCT 120/refractometer 130 ensemble. The beam splitter 152b can direct light between a display 160 and the binocular 117. A third beam splitter 152a can direct light to the camera 118.

The analyzer, or controller, 140 can perform the integrated biometrical analysis based on the received OCT and refractive information. The analysis can make use of a wide variety of well-known optical software systems and products, including ray tracing software and computer-aided design (CAD) software. The result of the integrated biometry can be (1) a value of the optical power of portions of the eye and a corresponding suggested or prescribed diopter for a suitable IOL; (2) a value and an orientation of an astigmatism of the cornea, and suggested or prescribed toric parameters of a toric IOL to compensate this astigmatism; and (3) a suggested or prescribed location and length of one or more relaxing incisions to correct this astigmatism, among others.

The analyzer 140 can output the result of this integrated biometry to the display 160, so that the display 160 can display these results for the surgeon. Display 160 can be an electronic video-display or a computerized display, associated with the eye-visualization system 110. In other embodiments, the display 160 can be a display in close proximity of the microscope 112, such as attached to the outside of the microscope 112. Finally, in some embodiments, display 160 can be a micro-display, or heads-up display, that projects the display light into the optical pathway of the microscope 112. The projection can be coupled into the main optical pathway via a mirror 157. In other embodiments, the entire heads-up display 160 can be located inside the microscope 112, or integrated with a port of the microscope 112.

Anatomically, the iris 18 is in contact or in close proximity to the crystalline or lens 14 and/or lens capsule surrounding the lens 14, which can cause difficulties when only the lens information is of interest to the user. For instance, when building a customized eye model, it is crucial to include the shape of the anterior lens. However, with the iris 18 closely in contact with the lens surface, a mixture of the anterior iris and the anterior lens can be misinterpreted as the anterior lens, which can then undermine the performance of the eye model. Therefore, in order to extract the lens information accurately, one should detect the iris.

Iris detection, which includes detecting the edge of the iris 18, has primarily been done by examining the OCT signal strength. In normal eyes, the OCT signal of the iris 18 is often stronger than that of other tissues around it. However, in pathological eyes, such as dense cataract, the OCT signal of the lens 14 can be strong as well. Therefore, iris detection based on OCT signal strength is not robust enough in clinical settings, where a variety of cataract conditions occur in the eye. The thickness of the iris 18, in combination with the OCT signal strength, may also be used for iris detection. However, depending on the size of the pupil, the thickness of the iris 18 changes too. Also, the thickness of the iris 18 varies substantially from person to person.

Accordingly, the previous methods for iris detection do not provide robust detection. The techniques disclosed herein use OCT measurements to exploit the intrinsic physical property difference between iris 18 and lens 14, and can therefore provide robust detection result of the iris's edge in clinical settings.

Figure 3:
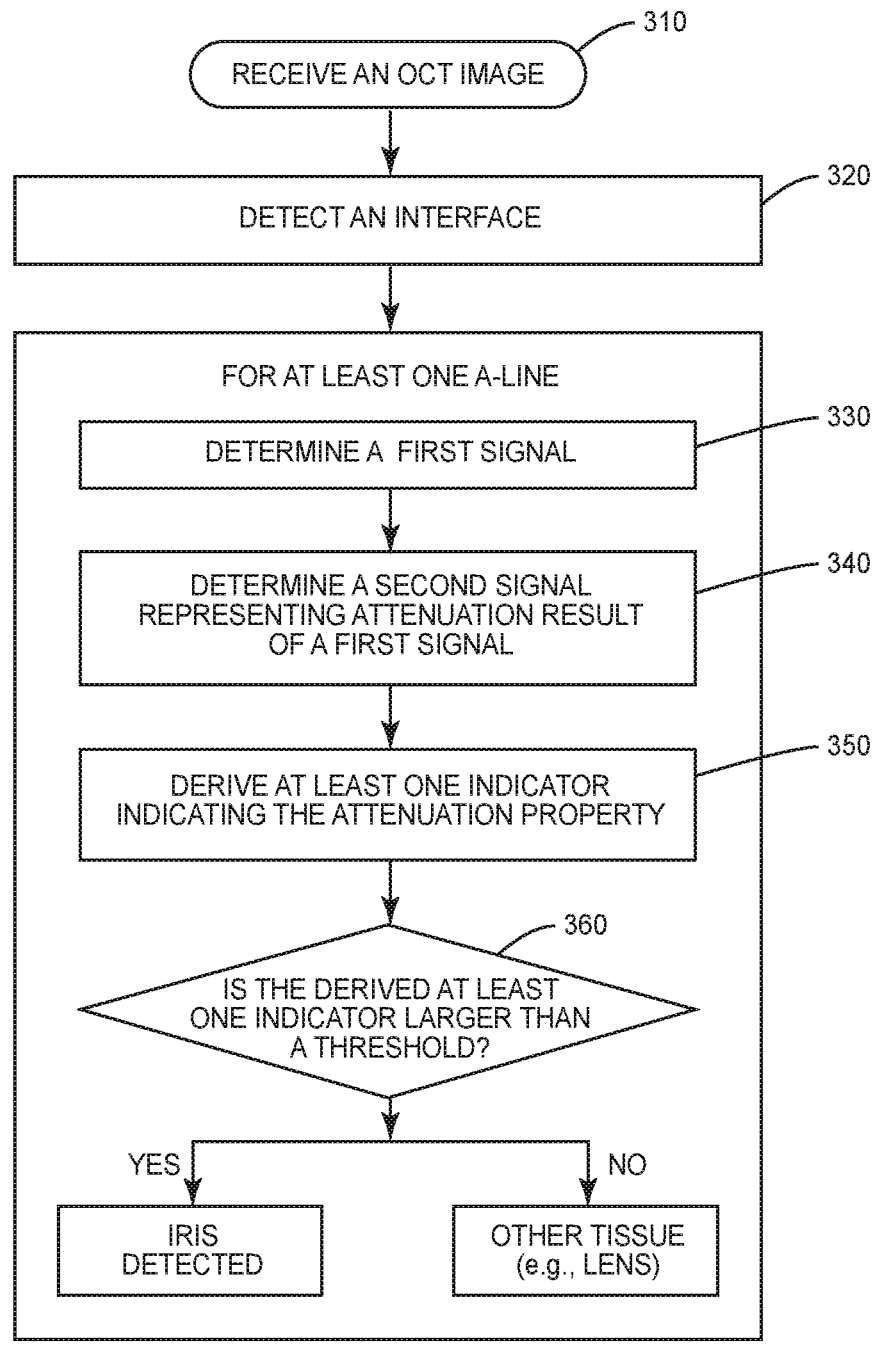
FIG. 3 is a process flow diagram illustrating an example method for iris detection.

FIG. 3 is a flow chart illustrating an example method for detecting an edge of an iris in OCT imaging of an eye 10, according to the presently disclosed techniques. First, as shown at block 310, an OCT image is received for iris detection. This comprises obtaining OCT data obtained from a scan of the eye 10, the OCT data comprising a plurality of A-lines, some of which pass through the iris 18 and the lens 14 of the eye 10 and some of which pass through the lens 14 but not the iris 18.

Then, as shown at block 320, at least a first interface is detected, where this first interface extends across adjacent A-lines. At least a portion of this detected first interface is assumed to correspond to the anterior surface of the iris or the posterior surface of the iris, but some portions of it may instead correspond to the lens. As will be discussed in further detail below, multiple interfaces may be detected at this stage of the method, in some embodiments. For instance, two interfaces can be detected, of which at least a portion of the first interface is the anterior surface of the iris 18 and at least a portion of the second interface is the posterior surface of the iris 18. More generally, multiple interfaces may be detected, where at least a portion of at least one of the multiple interfaces corresponds to the anterior surface of the iris or the posterior surface of the iris.

As shown at block 330, the method proceeds with the determining, for each of several adjacent A-lines, a first signal, corresponding to a point in the A-line that is before or during the attenuation by ocular tissues. This may comprise, for example, determining a first metric, e.g., average intensity, from one or more A-line pixels near the detected first interface, such that the first metric reflects an OCT signal intensity associated with the first interface.

Next, as shown at block 340, a second signal is determined for each of the several A-lines, where the second signal corresponds to the attenuation result of the first signal. More specifically, this may comprise determining, for each of the adjacent A-lines, a second metric derived from one or more A-line pixels further from the detected first interface than the one or more A-line pixels used to derive the first metric, such that the second metric reflects OCT signal attenuation at a point or points posterior to the detected first interface.

As shown at block 350, the method proceeds with the deriving of, for each of the several A-lines, at least one indicator indicating the attenuation property of at least one A-line, based on the first and second signals. More specifically, this may comprise calculating an attenuation parameter for each of the adjacent A-lines, based on the first and second metrics discussed above.

This derived indicator may then be compared to a threshold, as shown at block 360, to determine whether the iris is detected, for each of the several A-lines. In other words, the method may include determining, for each of the adjacent A-lines, whether the A-line passes through the iris, by comparing the attenuation parameter discussed above to a threshold value. It will be appreciated that the edge of the iris may be detected by observing which A-lines pass through the iris (and the lens) and which pass through the lens but not through the iris.

It will be understood that a derived indicator of attenuation can be chosen so that when the at least one indicator is larger than a threshold, the corresponding A-line is deemed to have passed through the iris. It is also possible to choose the at least one indicator so that when the at least one indicator is smaller or equal than a threshold, it indicates the iris. It is further to be understood that the threshold used is not limited to a fixed value. The threshold can be adaptive between different A-lines or different OCT images.

Figure 4:
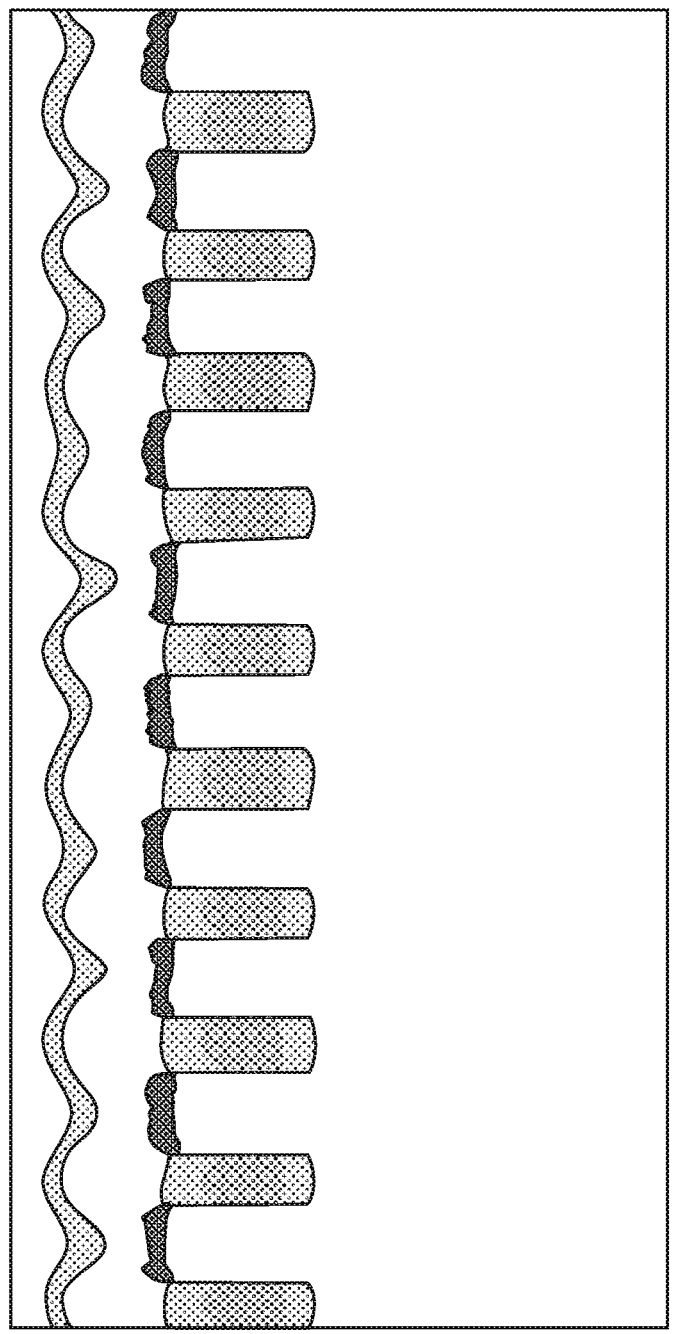
FIG. 4 illustrates an example OCT image.

FIGS. 4-10 illustrate an example use of the method illustrated in FIG. 3 and discussed above. FIG. 4 illustrates an example OCT image comprising many A-lines indexed from left to right, where A-lines extend from the top of the image to the bottom. It is noteworthy that the techniques described herein on any OCT scan pattern, such as line scan, raster scan, circular scan, spiral scan, lissajous scan, a flower scan, etc. FIG. 11 illustrates the scan pattern used to obtain the OCT image of FIG. 4. The scan starts at one point of the scan pattern and proceeds through each petal of the pattern, until coming back to the same point.

In FIG. 4, the high intensity reflections from the cornea can be seen at the top of the image. Below (posterior to) that can be seen reflection data corresponding to the iris and the lens. The challenge, as discussed above, is to determine where the edge of the iris is, so that the shape of the lens can be accurately determined.

Figure 5:
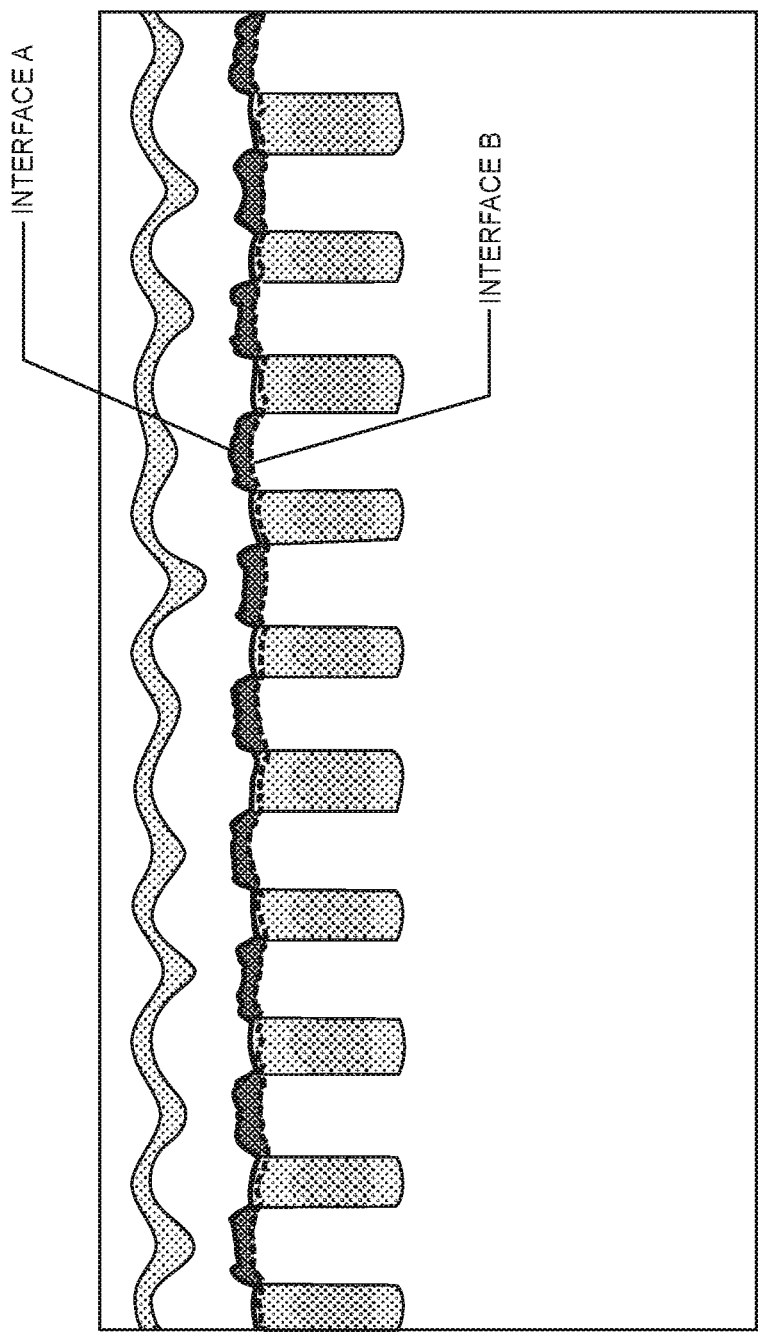
FIG. 5 shows the result of detecting interfaces in the OCT image of FIG. 4.

FIG. 5 shows the result of detecting interface based on the example OCT image in FIG. 4. In this specific example, two interfaces were detected, identified in the figure as interface A and interface B. Portions of interface A correspond to the anterior surface of the iris, while other portions extend across the lens. Likewise, portions of the interface B correspond to the posterior surface of the iris, while other portions extend across the lens, e.g., along the inside of the lens capsule. As discussed above, with respect to block 330 of FIG. 3, one (e.g., interface A only or interface B only) or more interfaces can be detected in this step of the analysis.

Figure 6:
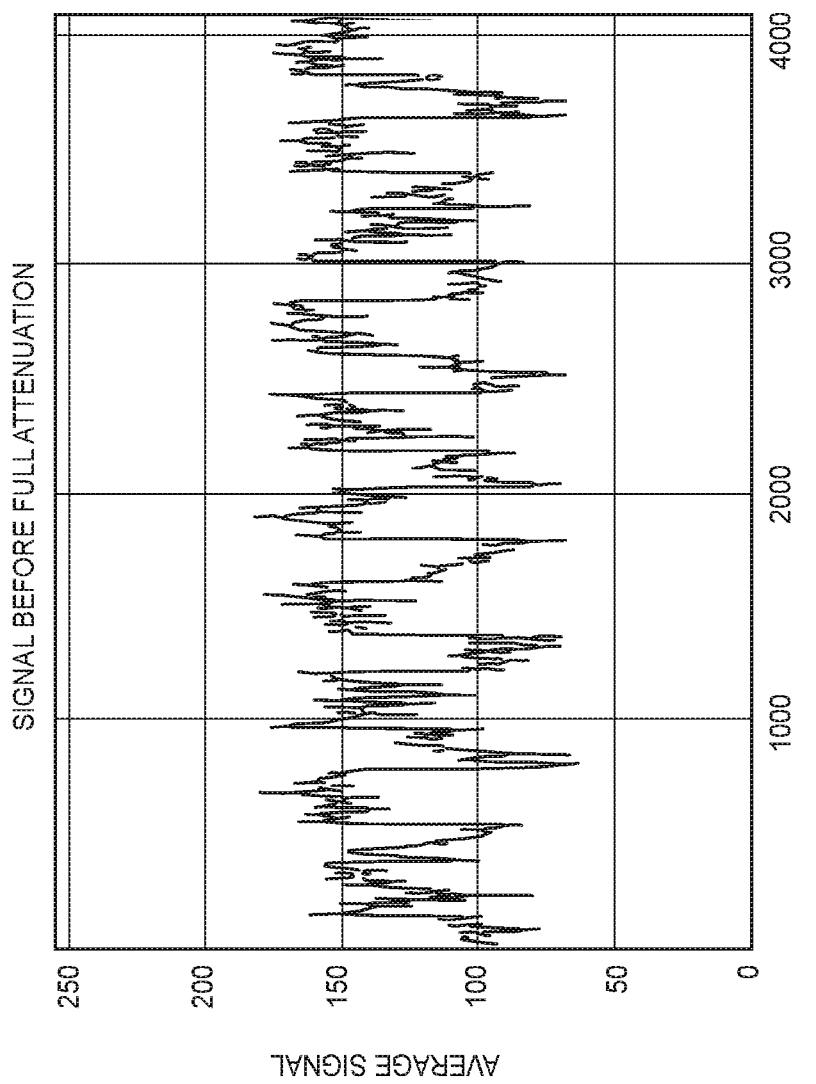
FIG. 6 illustrates example first signal metrics, based on the OCT image of FIG. 4.

FIG. 6 illustrates a graph of a first signal metric for each of the A-lines in FIGS. 4 and 5. This first metric reflects an OCT signal intensity associated with the first interface. In this example, the first signal metric is the average OCT intensity between the detected first interface (interface A) and the second interface (interface B). In other examples, the first signal metric can be OCT intensity at certain number of pixels (e.g., two pixels, five pixels, ten pixels) below the first interface. In yet another example, the first signal metric can be OCT intensity at a certain number of pixels (e.g., two pixels, five pixels, ten pixels) above the second interface. In yet another example, the first signal can be the maximum OCT intensity metric between the first interface and second interface.

Figure 7:
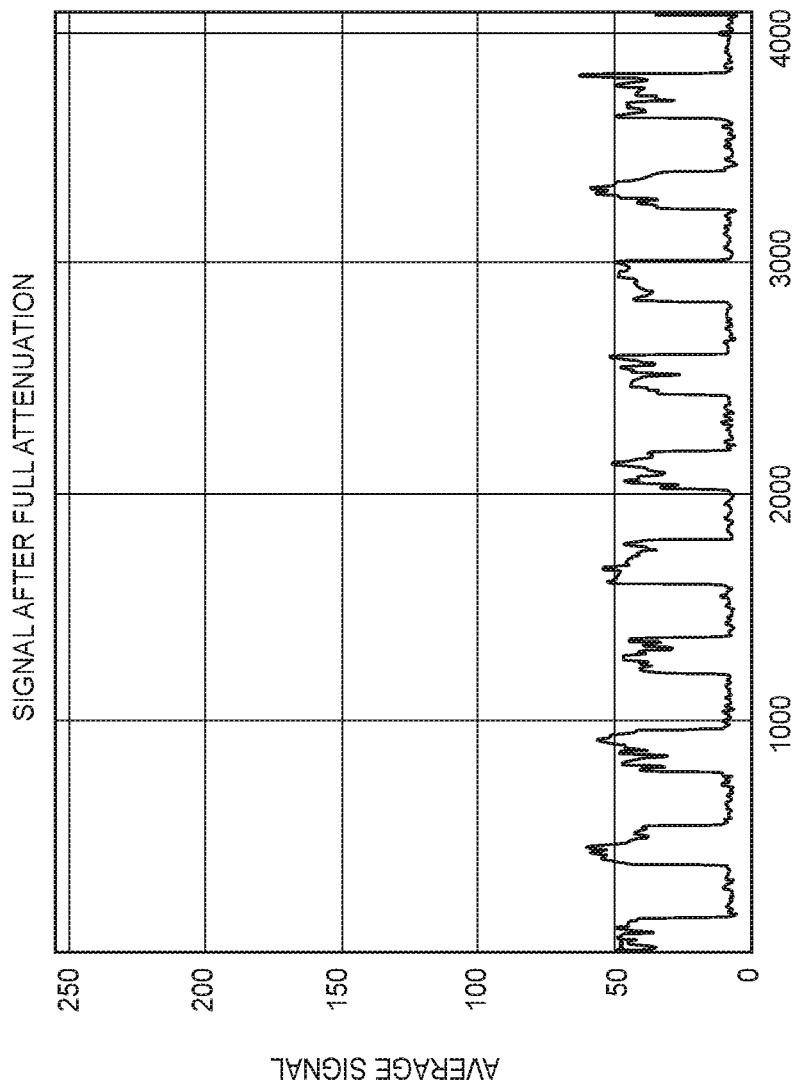
FIG. 7 illustrates example second signal metrics, based on the OCT image of FIG. 4.

FIG. 7 illustrates a graph of a second signal metric, representing the attenuation result of the first signal. This second metric thus reflects OCT signal attenuation at a point or points posterior to the detected first interface. In this specific example, the second signal is the average OCT intensity below the second interface (interface B).

Figure 8:
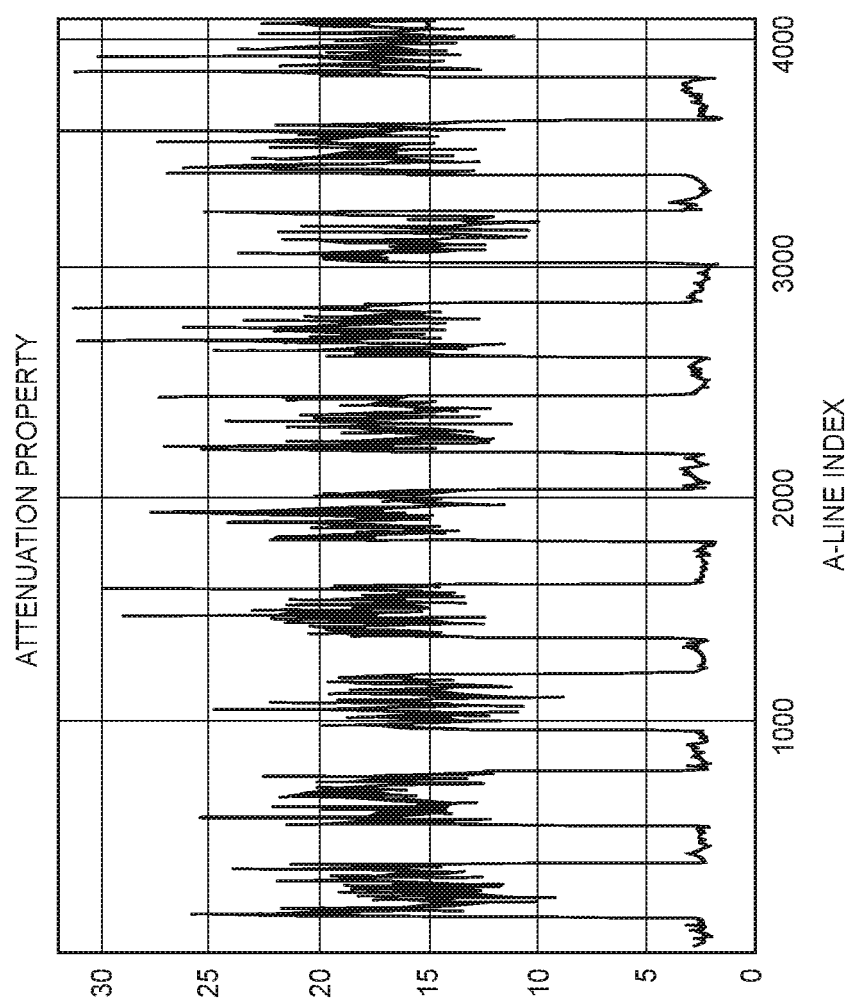
FIG. 8 illustrates an example graph of attenuation parameters, based on the first and second signal metrics of FIGS. 5 and 6.

Based on the determined first and second metrics, an attenuation property along each A-line of interest can be derived. In other words, an attenuation parameter can be calculated for each of the adjacent A-lines, based on the first and second metrics. FIG. 8 illustrates a graph of an example attenuation parameter for each A-line. In this example, the attenuation parameter is calculated as the ratio between the first signal metric and the second signal metric. Other parameters can also be used to represent the attenuation feature of the tissue, such as the difference between the first signal metric and the second signal metric. The attenuation parameter values for each of the A-lines may also be determined by curve fitting to the first and second signal metrics, for example.

Figure 9:
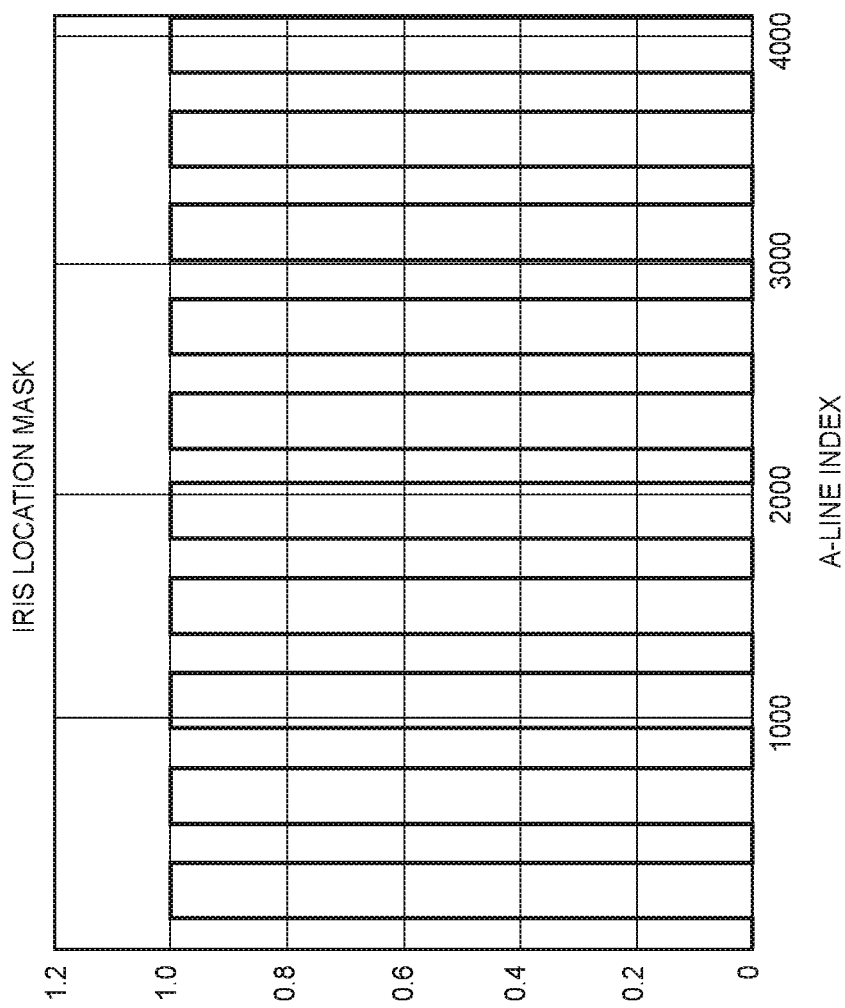
FIG. 9 illustrates an example iris location mask, obtained by comparing the attenuation parameters of FIG. 8 to a threshold.

Once the attenuation indicator is obtained, the iris location can be detected by comparing the derived at least one indicator to a threshold. The results of this comparison can be used to generate an iris location mask, as shown in FIG. 9, which precisely reveals the edge of the iris. In this specific example, a threshold of 5 is used to differentiate iris from lens. Other appropriate thresholds, either constant or adaptive, can also be used to detect iris.

Figure 10:
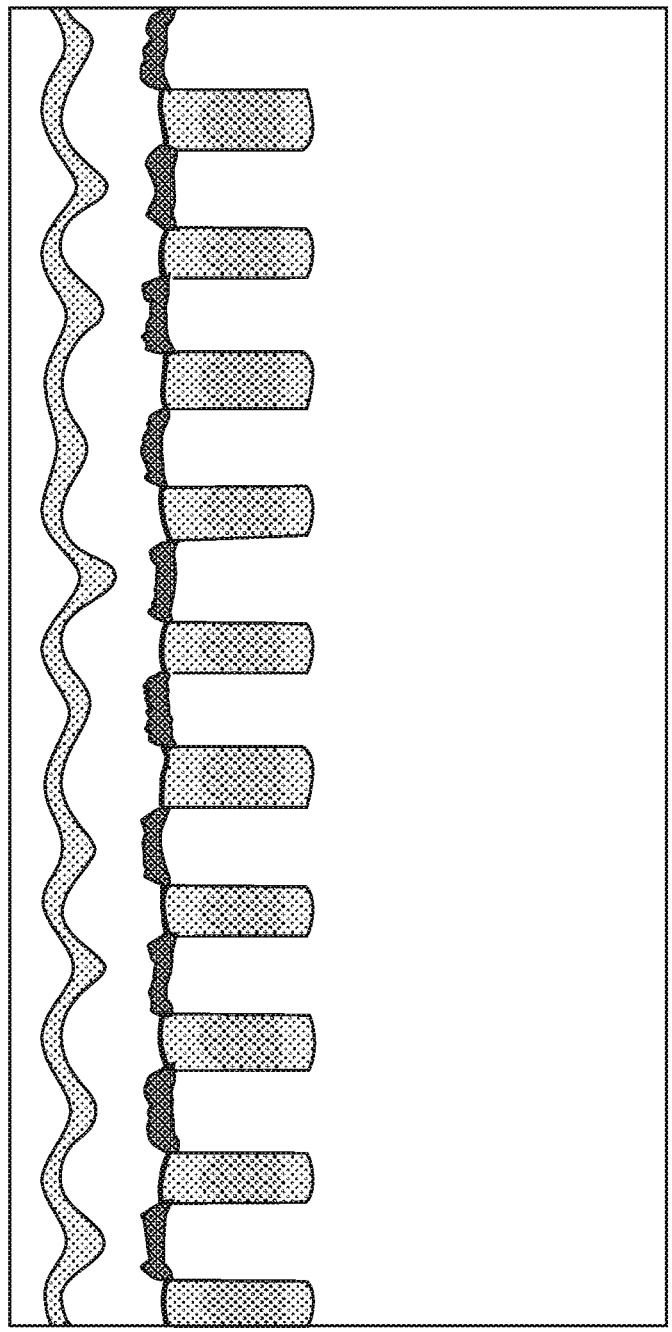
FIG. 10 illustrates a segmentation result superimposed on the OCT image data from FIG. 4.
Figure 11:
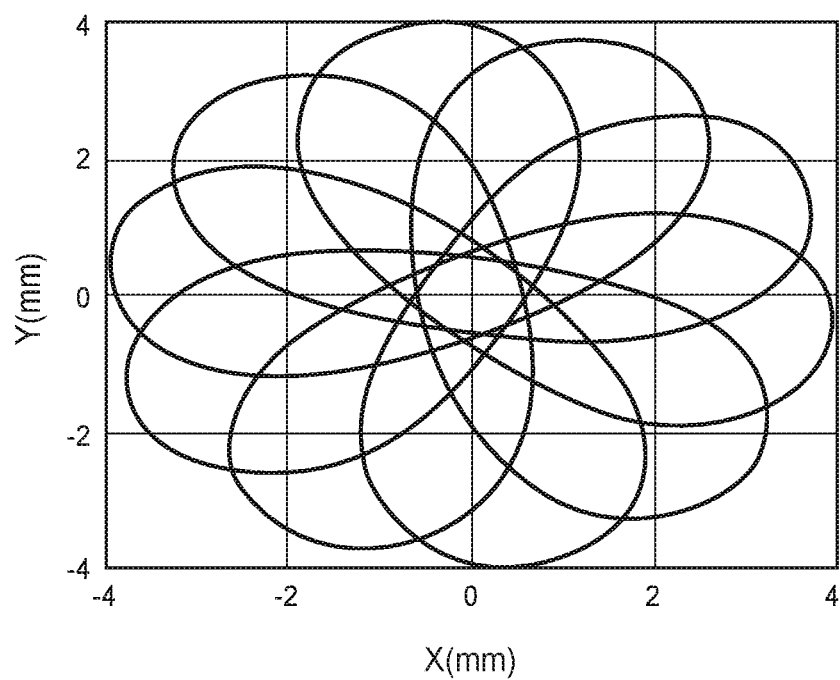
FIG. 11 illustrates an example OCT scan pattern.

FIG. 10 illustrates the final segmentation result combined with iris detection, based on the mask from FIG. 9. Because the iris is accurately detected, the segmented interface represents the true geometry of the anterior surface of the lens, rather than a mixture of the anterior surface of the iris and the anterior surface of the lens, as was present in interface B, as shown in FIG. 5.

Figure 12:
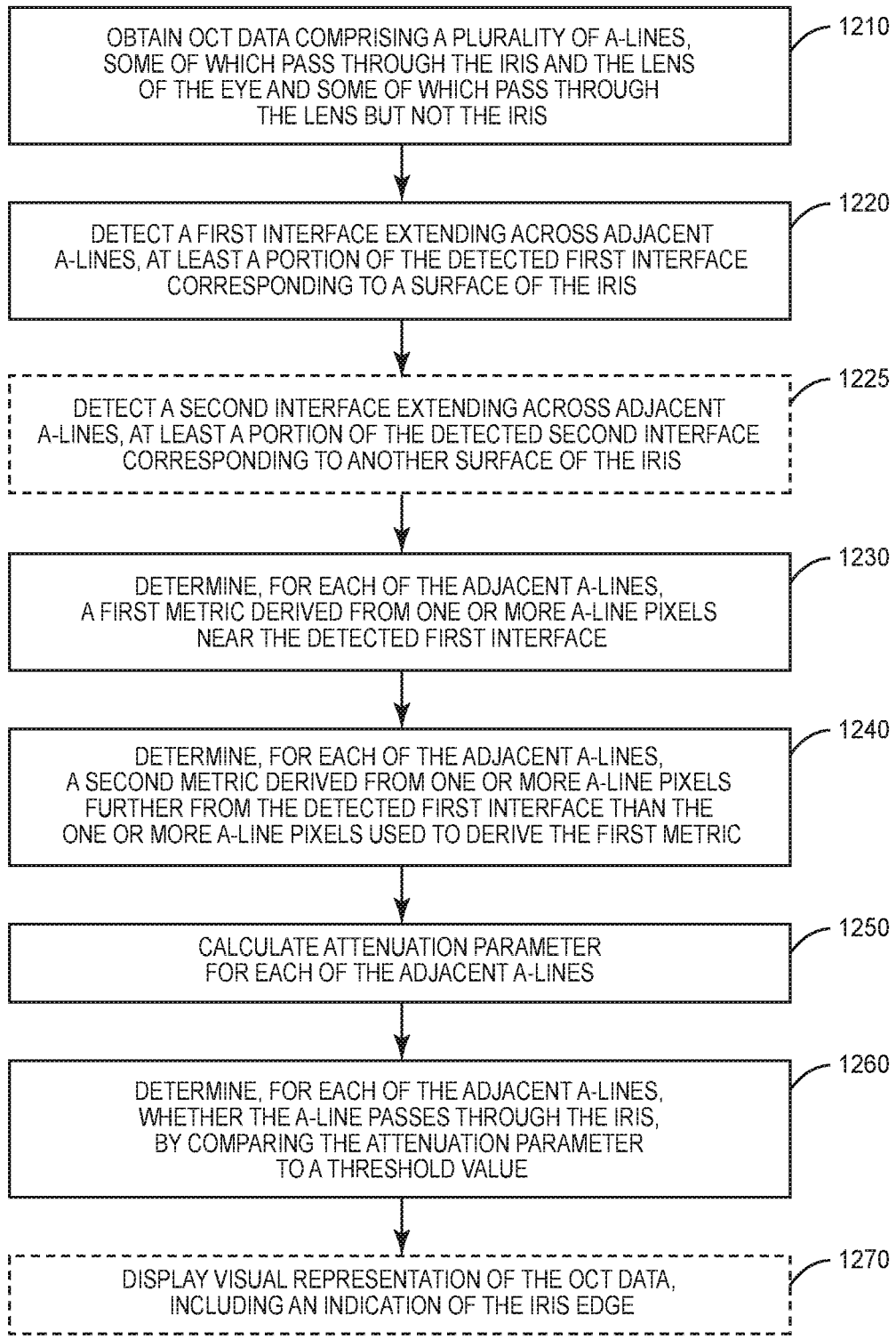
FIG. 12 is another process flow diagram illustrating an example method for iris detection.

In view of the detailed explanation and examples provided above, it will be appreciated that the process flow illustrated in FIG. 12 represents an example method for detecting an edge of an iris in OCT imaging of an eye, according to the techniques disclosed herein. This method corresponds generally to the method illustrated in FIG. 3.

As shown at block 1210, the illustrated method includes obtaining OCT data obtained from a scan of the eye, the OCT data comprising a plurality of A-lines, some of which pass through the iris and the lens of the eye and some of which pass through the lens but not the iris. As shown at block 1220, the method further comprises detecting a first interface extending across adjacent A-lines, where at least a portion of the interface is assumed to correspond to either the anterior surface or posterior surface of the iris.

As shown at block 1230, the method further includes determining, for each of the adjacent A-lines, a first metric derived from one or more A-line pixels near the detected first interface, such that the first metric reflects an OCT signal intensity associated with the first interface. In some embodiments or instances, at least a portion of the detected first interface is assumed to correspond to the anterior surface of the iris, and the first metric is determined for each of the adjacent A-lines by selecting an A-line pixel value at a predetermined number of A-line pixels below the detected first interface. In other embodiments or instances, at least a portion of the detected first interface is assumed to correspond to the anterior surface of the iris, and the first metric is determined for each of the adjacent A-lines by calculating an average A-line pixel value for a range of A-line pixels beginning at a predetermined number of A-line pixels below the detected first interface. In still other embodiments or instances, at least a portion of the detected first interface is assumed to correspond to the posterior surface of the iris, and the first metric is determined for each of the adjacent A-lines by selecting an A-line pixel value at a predetermined number of A-line pixels above the detected first interface. In yet other embodiments or instances, at least a portion of the detected first interface is assumed to correspond to the posterior surface of the iris, and the first metric is determined for each of the adjacent A-lines by calculating an average A-line pixel value for a range of A-line pixels beginning at a predetermined number of A-line pixels above the detected first interface. In still others, the first metric is determined based on one or more pixel values between the detected first interface and a second detected interface. Other variations of these approaches for determining a first metric that reflects an OCT signal intensity associated with the first interface are possible.

As shown at block 1240, the method further includes determining, for each of the adjacent A-lines, a second metric derived from one or more A-line pixels further from the detected first interface than the one or more A-line pixels used to derive the first metric, such that the second metric reflects OCT signal attenuation at a point or points posterior to the detected first interface. In some embodiments, for example, the second metric is determined for each of the adjacent A-lines by calculating a median or mean of A-line pixels for a range of A-line pixels posterior to the detected first interface.

In some embodiments, at least a portion of the detected first interface is assumed to correspond to the anterior surface of the iris, and the method further comprises detecting a second interface extending across the adjacent A-lines, where at least a portion of the detected second interface is assumed to correspond to the posterior surface of the iris. This is shown in FIG. 12 at block 1225, which is illustrated with a dashed outline to indicate that it need not be present in every instance or embodiment of the illustrated method. In some of these embodiments, the first metric may be determined (as illustrated at block 1230) for each of the adjacent A-lines by calculating a median, mean, or maximum of A-line pixel values for A-line pixels between the detected first and second interfaces. In some of these embodiments, the second metric may be determined (as illustrated at block 1240) for each of the adjacent A-lines by calculating a median or mean of A-line pixels for a range of A-line pixels posterior to the detected second interface.

As shown at blocks 1250 and 1260, the illustrated method further comprises calculating an attenuation parameter for each of the adjacent A-lines, based on the first and second metrics, and determining, for each of the adjacent A-lines, whether the A-line passes through the iris, by comparing the attenuation parameter to a threshold value. Calculating the attenuation parameter for each of the adjacent A-lines may comprise calculating the difference between the first and second metrics, wherein the attenuation parameter is based on the calculated difference, or calculating a ratio of the first and second metrics, wherein the attenuation parameter is based on the calculated ratio, for example. In some embodiments, calculating the attenuation parameter may comprise smoothing these calculated differences or calculated ratios, such that the attenuation parameters are based on the smoothed calculated differences or smoothed calculated ratios. In some embodiments, the attenuation parameters may be obtained by fitting a curve to the calculated differences or calculated ratios.

In some embodiments, the method further comprises displaying a visual representation of the OCT data, the visual representation including an indication of the iris edge, based on the determining, for each A-line, of whether the A-line passes through the iris. This is shown in FIG. 12 at block 1270.

The techniques described herein may be performed using OCT image obtained from an OCT imaging apparatus, e.g., from an apparatus like that illustrated in FIG. 1. These techniques may be integrated into the OCT imaging apparatus itself, to produce an imaging system that integrates OCT imaging and the iris detection techniques described herein.

Accordingly, some embodiments of the present invention include an OCT image processing apparatus, the OCT image processing apparatus comprising a communications interface for obtaining OCT data obtained from a scan of the eye, and a processing circuit operatively coupled to the communications interface and configured out one or more of the techniques described herein. This OCT image processing apparatus may correspond to the analyzer/controller 140 pictured in FIG. 1, in some embodiments.

The OCT data obtained by the OCT image processing apparatus in these various embodiments comprises a plurality of A-lines, some of which pass through the iris and the lens of the eye and some of which pass through the lens but not the iris. The processing circuit may comprise one or more microprocessors, microcontrollers, or the like, and associated memory storing program code for execution by the microprocessors, microcontrollers, or the like, with the program code comprising computer program instructions for carrying out all or the techniques described herein, and may also or instead comprise other digital logic configured to carry out all or parts of any of the techniques described herein. The processing circuit is thereby configured to detect a first interface extending across adjacent A-lines, wherein at least a portion of the detected first interface is assumed to correspond to either the anterior surface or posterior surface of the iris, and determine, for each of the adjacent A-lines, a first metric derived from one or more A-line pixels near the detected first interface, such that the first metric reflects an OCT signal intensity associated with the first interface. The processing circuit is further configured to determine, for each of the adjacent A-lines, a second metric derived from one or more A-line pixels further from the detected first interface than the one or more A-line pixels used to derive the first metric, such that the second metric reflects OCT signal attenuation at a point or points posterior to the detected first interface, and calculate an attenuation parameter for each of the adjacent A-lines, based on the first and second metrics. The processing circuit is still further configured to determine, for each of the adjacent A-lines, whether the A-line passes through the iris, by comparing the attenuation parameter to a threshold value.

In some embodiments, the OCT image processing apparatus further comprises or is associated with a video display, e.g., the display 160 illustrated in FIG. 1, and the processing circuit is further configured to use or cause the display to display a visual representation of the OCT data, the visual representation including an indication of the iris edge, based on the determining, for each A-line, of whether the A-line passes through the iris.

The OCT image processing apparatus described above may be configured to carry out one or several of the variants of the techniques described above, in various embodiments. Accordingly, in some embodiments of the OCT image processing apparatus, at least a portion of the detected first interface is assumed to correspond to the anterior surface of the iris, and the processing circuit is configured to determine the first metric for each of the adjacent A-lines by selecting an A-line pixel value at a predetermined number of A-line pixels below the detected first interface. In other embodiments, at least a portion of the detected first interface is assumed to correspond to the anterior surface of the iris, and the processing circuit is configured to determine the first metric for each of the adjacent A-lines by calculating an average A-line pixel value for a range of A-line pixels beginning at a predetermined number of A-line pixels below the detected first interface. In still other embodiments, at least a portion of the detected first interface is assumed to correspond to the posterior surface of the iris, and the processing circuit is configured to determine the first metric for each of the adjacent A-lines by selecting an A-line pixel value at a predetermined number of A-line pixels above the detected first interface. In yet other embodiments, at least a portion of the detected first interface is assumed to correspond to the posterior surface of the iris, and the processing circuit is configured to determine the first metric for each of the adjacent A-lines by calculating an average A-line pixel value for a range of A-line pixels beginning at a predetermined number of A-line pixels above the detected first interface.

In some embodiments, the processing circuit is configured to determine the second metric for each of the adjacent A-lines by calculating a median or mean of A-line pixels for a range of A-line pixels posterior to the detected first interface. In some embodiments, at least a portion of the detected first interface is assumed to correspond to the anterior surface of the iris, and the processing circuit is configured to detect a second interface extending across the adjacent A-lines, where at least a portion of the detected second interface is assumed to correspond to the posterior surface of the iris. In some of these embodiments, the processing circuit is configured to determine the first metric for each of the adjacent A-lines by calculating a median, mean, or maximum of A-line pixel values for A-line pixels between the detected first and second interfaces. In some of these latter embodiments, the processing circuit is configured to determine the second metric for each of the adjacent A-lines by calculating a median or mean of A-line pixels for a range of A-line pixels posterior to the detected second interface.

In some of the embodiments described above, the processing circuit is configured to calculate the attenuation parameter for each of the adjacent A-lines based on one of: the difference between the first and second metrics; and a ratio of the first and second metrics. In some embodiments, the processing circuit is configured to smooth the calculated differences or calculated ratios, and calculate the attenuation parameters based on the smoothed calculated differences or smoothed calculated ratios. In some embodiments, the attenuation parameters are obtained by fitting a curve to the calculated differences or calculated ratios.

The specific embodiments described above illustrate but do not limit the invention. It should also be understood that numerous modifications and variations are possible in accordance with the principles of the present invention, as described above and as claimed below.

What is claimed is:

1. A method for detecting an edge of an iris in optical coherence tomography (OCT) imaging of an eye, the method comprising:
    obtaining OCT data obtained from a scan of the eye, the OCT data comprising a plurality of A-lines, some of which pass through the iris and the lens of the eye and some of which pass through the lens but not the iris;
    detecting a first interface extending across adjacent A-lines, wherein at least a portion of the detected first interface is assumed to correspond to either the anterior surface or posterior surface of the iris;
    determining, for each of the adjacent A-lines, a first metric derived from one or more A-line pixels near the detected first interface, such that the first metric reflects an OCT signal intensity associated with the first interface;
    determining, for each of the adjacent A-lines, a second metric derived from one or more A-line pixels further from the detected first interface than the one or more A-line pixels used to derive the first metric, such that the second metric reflects OCT signal attenuation at a point or points posterior to the detected first interface;
    calculating an attenuation parameter for each of the adjacent A-lines, based on the first and second metrics; and
    determining, for each of the adjacent A-lines, whether the A-line passes through the iris, by comparing the attenuation parameter to a threshold value.

2. The method of claim 1, wherein at least a portion of the detected first interface is assumed to correspond to the anterior surface of the iris, and wherein the first metric is determined for each of the adjacent A-lines by selecting an A-line pixel value at a predetermined number of A-line pixels below the detected first interface.

3. The method of claim 1, wherein at least a portion of the detected first interface is assumed to correspond to the anterior surface of the iris, and wherein the first metric is determined for each of the adjacent A-lines by calculating an average A-line pixel value for a range of A-line pixels beginning at a predetermined number of A-line pixels below the detected first interface.

4. The method of claim 1, wherein at least a portion of the detected first interface is assumed to correspond to the posterior surface of the iris, and wherein the first metric is determined for each of the adjacent A-lines by selecting an A-line pixel value at a predetermined number of A-line pixels above the detected first interface.

5. The method of claim 1, wherein at least a portion of the detected first interface is assumed to correspond to the posterior surface of the iris, and wherein the first metric is determined for each of the adjacent A-lines by calculating an average A-line pixel value for a range of A-line pixels beginning at a predetermined number of A-line pixels above the detected first interface.

6. The method of claim 1, wherein the second metric is determined for each of the adjacent A-lines by calculating a median or mean of A-line pixels for a range of A-line pixels posterior to the detected first interface.

7. The method of claim 1, wherein at least a portion of the detected first interface is assumed to correspond to the anterior surface of the iris, the method further comprising detecting a second interface extending across the adjacent A-lines, wherein at least a portion of the detected second interface is assumed to correspond to the posterior surface of the iris, and wherein the first metric is determined for each of the adjacent A-lines by calculating a median, mean, or maximum of A-line pixel values for A-line pixels between the detected first and second interfaces.

8. The method of claim 7, wherein the second metric is determined for each of the adjacent A-lines by calculating a median or mean of A-line pixels for a range of A-line pixels posterior to the detected second interface.

9. The method of claim 1, wherein calculating the attenuation parameter for each of the adjacent A-lines comprises one of:
calculating the difference between the first and second metrics, wherein the attenuation parameter is based on the calculated difference; and
calculating a ratio of the first and second metrics, wherein the attenuation parameter is based on the calculated ratio.

10. The method of claim 9, wherein calculating the attenuation parameter comprises smoothing the calculated differences or calculated ratios, wherein the attenuation parameters are based on the smoothed calculated differences or smoothed calculated ratios.

11. The method of claim 9, wherein the attenuation parameters are obtained by fitting a curve to the calculated differences or calculated ratios.

12. The method of claim 1, further comprising displaying a visual representation of the OCT data, the visual representation including an indication of the iris edge, based on the determining, for each A-line, of whether the A-line passes through the iris.

13. An Optical Coherence Tomography (OCT) imaging apparatus, comprising:
a communication interface configured to obtain OCT data obtained from a scan of the eye, the OCT data comprising a plurality of A-lines, some of which pass through the iris and the lens of the eye and some of which pass through the lens but not the iris; and
a processing circuit operatively coupled to the communication interface and configured to:
detect a first interface extending across adjacent A-lines, wherein at least a portion of the detected first interface is assumed to correspond to either the anterior surface or posterior surface of the iris;
determine, for each of the adjacent A-lines, a first metric derived from one or more A-line pixels near the detected first interface, such that the first metric reflects an OCT signal intensity associated with the first interface;
determine, for each of the adjacent A-lines, a second metric derived from one or more A-line pixels further from the detected first interface than the one or more A-line pixels used to derive the first metric, such that the second metric reflects OCT signal attenuation at a point or points posterior to the detected first interface;
calculate an attenuation parameter for each of the adjacent A-lines, based on the first and second metrics; and
determine, for each of the adjacent A-lines, whether the A-line passes through the iris, by comparing the attenuation parameter to a threshold value.

14. The OCT imaging apparatus of claim 13, wherein at least a portion of the detected first interface is assumed to correspond to the anterior surface of the iris, and wherein the processing circuit is configured to determine the first metric for each of the adjacent A-lines by selecting an A-line pixel value at a predetermined number of A-line pixels below the detected first interface.

15. The OCT imaging apparatus of claim 13, wherein at least a portion of the detected first interface is assumed to correspond to the anterior surface of the iris, and wherein the processing circuit is configured to determine the first metric for each of the adjacent A-lines by calculating an average A-line pixel value for a range of A-line pixels beginning at a predetermined number of A-line pixels below the detected first interface.

16. The OCT imaging apparatus of claim 13, wherein at least a portion of the detected first interface is assumed to correspond to the posterior surface of the iris, and wherein the processing circuit is configured to determine the first metric for each of the adjacent A-lines by selecting an A-line pixel value at a predetermined number of A-line pixels above the detected first interface.

17. The OCT imaging apparatus of claim 13, wherein at least a portion of the detected first interface is assumed to correspond to the posterior surface of the iris, and wherein the processing circuit is configured to determine the first metric for each of the adjacent A-lines by calculating an average A-line pixel value for a range of A-line pixels beginning at a predetermined number of A-line pixels above the detected first interface.

18. The OCT imaging apparatus of claim 13, wherein the processing circuit is configured to determine the second metric for each of the adjacent A-lines by calculating a median or mean of A-line pixels for a range of A-line pixels posterior to the detected first interface.

19. The OCT imaging apparatus of claim 13, wherein at least a portion of the detected first interface is assumed to correspond to the anterior surface of the iris, and wherein the processing circuit is further configured to detect a second interface extending across the adjacent A-lines, wherein at least a portion of the detected second interface is assumed to correspond to the posterior surface of the iris, and wherein the processing circuit is configured to determine the first metric for each of the adjacent A-lines by calculating a median, mean, or maximum of A-line pixel values for A-line pixels between the detected first and second interfaces.

20. The OCT imaging apparatus of claim 19, wherein the processing circuit is configured to determine the second metric for each of the adjacent A-lines by calculating a median or mean of A-line pixels for a range of A-line pixels posterior to the detected second interface.

21. The OCT imaging apparatus of claim 13, wherein the processing circuit is configured to calculate the attenuation parameter for each of the adjacent A-lines based on one of:
the difference between the first and second metrics; and
a ratio of the first and second metrics.

22. The OCT imaging apparatus of claim 21, wherein the processing circuit is configured to smooth the calculated differences or calculated ratios and calculate the attenuation parameters based on the smoothed calculated differences or smoothed calculated ratios.

23. The OCT imaging apparatus of claim 21, wherein the processing circuit is configured to obtain the attenuation parameters by fitting a curve to the calculated differences or calculated ratios.

24. The OCT imaging apparatus of claim 13, further comprising a display, wherein the processing circuit is configured to use or cause the display to display a visual representation of the OCT data, the visual representation including an indication of the iris edge, based on the determining, for each A-line, of whether the A-line passes through the iris.

* * * * *

UNITED STATES PATENT AND TRADEMARK OFFICE
CERTIFICATE OF CORRECTION

PATENT NO. : 10,827,921 B2
APPLICATION NO. : 16/202271
DATED : November 10, 2020
INVENTOR(S) : Hugang Ren and Muhammad K. Al-Qaisi It is certified that error appears in the above-identified patent and that said Letters Patent is hereby corrected as shown below:

On the Title Page

(71) Applicant, "Novartis AG, Basel (CH)" should be changed to --Alcon Inc., Fribourg (CH)--.

Signed and Sealed this
Twenty-second Day of December, 2020

Andrei Iancu
*Director of the United States Patent and Trademark Office*